United States Patent [19]
Bonnet et al.

[11] Patent Number: 6,121,432
[45] Date of Patent: Sep. 19, 2000

[54] ERYTHROMYCINS

[75] Inventors: Alain Bonnet, Chateau Thierry; Francoise Gambier, Paris, both of France

[73] Assignee: Hoechst Marion Roussel, France

[21] Appl. No.: 09/273,846

[22] Filed: Mar. 22, 1999

[30]    Foreign Application Priority Data

Apr. 8, 1998 [FR] France ..................... 98 04366

[51] Int. Cl.[7] .......................... C07H 17/08; A61K 31/70
[52] U.S. Cl. .............................. 536/7.2; 514/29
[58] Field of Search ................ 514/29; 536/7.2

[56]    References Cited

U.S. PATENT DOCUMENTS

| | | | |
|---|---|---|---|
| 4,740,502 | 4/1988 | Hannick et al. | 514/29 |
| 4,742,049 | 5/1988 | Baker et al. | 514/29 |
| 5,444,051 | 8/1995 | Agouridas et al. | 514/29 |
| 5,561,118 | 10/1996 | Agouridas et al. | 514/29 |
| 5,591,837 | 1/1997 | Asaka et al. | 536/7.4 |
| 5,631,354 | 5/1997 | Asaka et al. | 536/7.4 |
| 5,747,467 | 5/1998 | Agouridas et al. | 514/29 |
| 5,770,579 | 6/1998 | Agourdas et al. | 514/29 |

FOREIGN PATENT DOCUMENTS

| | | |
|---|---|---|
| 0487411 | 5/1992 | European Pat. Off. . |
| 0799833 | 10/1997 | European Pat. Off. . |

OTHER PUBLICATIONS

"Glossary of Class Names of Organic Compounds", IUPAC—Pure and Applied Chemistry, vol. 67: 1307–1375, 1995.

*Primary Examiner*—Howard C. Lee
*Attorney, Agent, or Firm*—Bierman, Muserlian and Lucas

[57]    ABSTRACT

Novel compounds of the formula

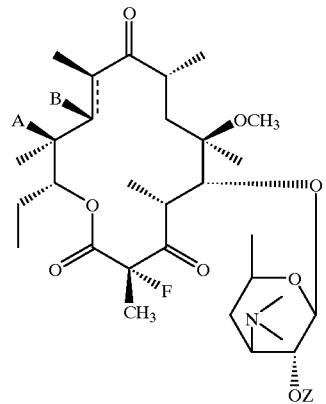

I wherein A is —OH and B forms with the 10-carbon a carbon—carbon double bond or A and B together form a carbonate or a carbamate, —OZ is selected from the group consisting of —OH, etherified hydroxy or esterified hydroxy and its non-toxic, pharmaceutically acceptable acid addition salts.

5 Claims, No Drawings

ERYTHROMYCINS

OBJECTS OF THE INVENTION

It is an object of the invention to provide the compounds of formula I and their acid addition salts and a process for their preparation.

It is another object of the invention to provide a process for the preparation of compounds of formula III and novel intermediates therefor.

These and other objects and advantages of the invention will become obvious from the following detailed description.

THE INVENTION

The novel compounds of the invention are selected from the group consisting of

I

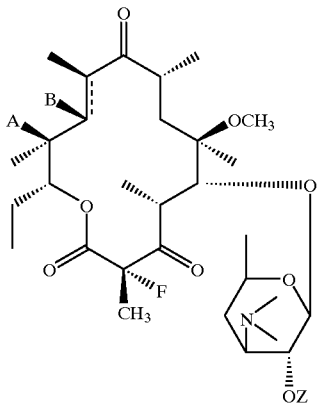

wherein A is —OH and B forms with the 10-carbon a carbon—carbon double bond or A and B together form a carbonate or a carbamate, —OZ is selected from the group consisting of —OH, etherified hydroxy or esterified hydroxy and its non-toxic, pharmaceutically acceptable acid addition salts.

Examples of organic and inorganic acids suitable for the non-toxic, pharmaceutically acceptable acid addition salts are hydrofluoric acid, hydrochloric acid, hydrobromic acid, hydroiodic acid, acetic acid, propionic acid, trifluoroacetic acid, maleic acid, tartaric acid, methanesulfonic acid, benzenesulfonic acid, p-toluenesulfonic acid, and especially stearic acid, ethylsuccinic acid or laurylsuccinic acid.

Preferably Z is hydrogen,

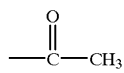

or trimethylsilyl and R is alkyl of 1 to 6 carbon atoms.

Preferred compounds of formula I are $I_A$

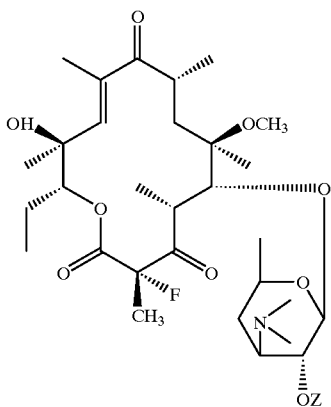

and $I_B$

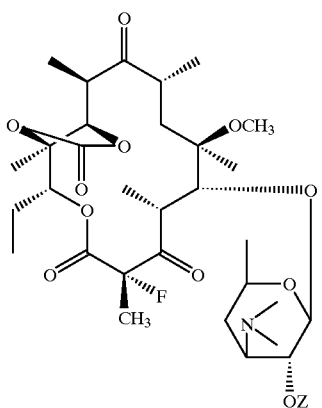

wherein Z is defined as above.

The process for the preparation of a compound of formula I comprises reacting a compound of the formula

A

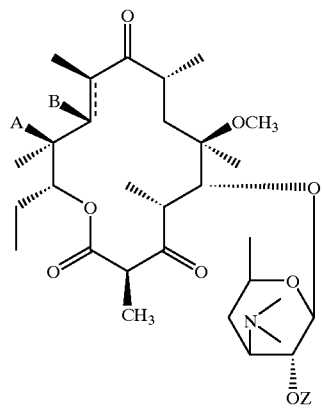

wherein A, B and —OZ are defined above with a fluoridation agent to obtain the compound of formula I, optionally releasing the 2'-hydroxyl and optionally esterifying or etherifying the 2'-hydroxyl and optionally forming A and B as a carbonate to form a compound of formula I$_A$ which optionally is subjected to an acid to form the acid addition salt.

The fluoridation agent may be N-fluoro-bis-(phenylsulfonyl)-imide of the formula

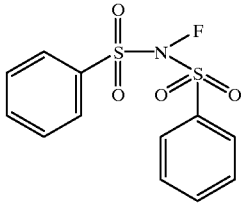

or any other electrophilic agents.

As an agent for releasing the 2'-hydroxyl, there can be mentioned strong bases such as tetrabutyl-ammonium fluoride when OZ is OSi(CH$_3$)$_3$ or alcohols such as methanol when OZ is COCH$_3$.

The process of the invention for preparing a compound of the formula

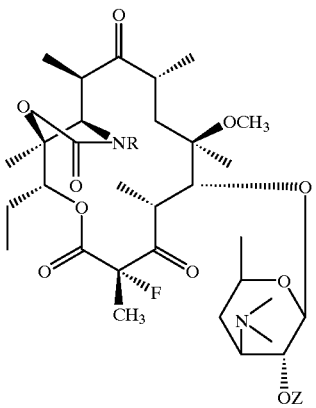

III comprises reacting a compound of formula I with carbonyl-diimidazole to form a compound of the formula

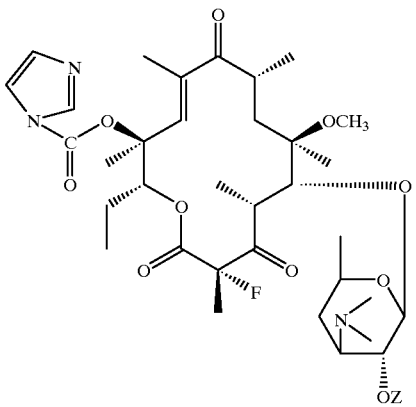

II and reacting the latter with an amine of the formula

R—NH$_2$ wherein R is alkyl of 1 to 6 carbon atoms to obtain a compound of formula III and optionally releasing the 2'-hydroxyl.

The compounds of formula II are novel and particularly, 12-(oxycarbonylimidazol)-11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-acetoxy-2α-fluoro.

In the following examples, there are described several preferred embodiments to illustrate the invention. However, it is to be understood that the invention is not intended to be limited to the specific embodiments.

EXAMPLE 1

3-de[(2,6-dideoxy-3-C-methyl-3-0-Methyl-α-L-ribohexopyranosyl)-oxy]-6-0-methyl-3-oxo-erythromycin-cyclic-2'-trimethylsilyloxy-2α-fluoro-11,12-carbonate 1.27 ml of a 1M solution of potassium terbutylate in THF were added at –78° C. to a solution of 685 mg of 3-de-[(2,6-dideoxy-3-C-methyl-3-0-methyl-α-L-ribohexopyranosyl)-oxy]-6-0-methyl-3-oxo-erythromycin-cyclic-2'-trimethylsilyloxy-11,12-carbonate and 10 ml of anhydrous THF. The mixture was stirred for 5 minutes at –78° C. and 389 mg of N-fluoro-benzene sulfonimide were added. The reaction mixture was held at –78° C. for 3 hours, followed by evaporation. Then, 5 ml of ethyl acetate, 5 ml of water of 0.5 ml of concentrated ammonium hydroxide were added and the reaction mixture was held at ambient temperature for 10 minutes and decanted. The organic phase was washed with water, followed by drying and evaporating to obtain the desired product.

NMR 250 MHz CDCl$_3$: H$_{13}$ (dd): 4.80; NMe$_2$ (s): 2.11; CH$_3$—C—F (d): 1.65 J=22 Hz; SiMe$_3$ (s): 0.02.

Preparation of the Starting Product of Example 1

6.14 g of 3-de-[(2,6-dideoxy-3-C-methyl-3-0-methyl-α-oxy]-6-0-methyl-3-oxo-erythromycin-cyclic-11,12-carbonate, 660 mg of imidazole, 62 ml of anhydrous THF and 2.05 ml of hexamethyl-disilylazane were stirred at ambient temperature for 4 days, followed by evaporation. The product was taken up with methylene chloride and sodium acid phosphate. The mixture was stirred for 15 minutes, followed by decanting, extraction with methylene chloride, drying and evaporation to obtain 5.02 g of the desired product.

NMR 250 MHz CDCl$_3$: H$_{13}$ (dd): 4.80; 6-OMe: 2.51 (S), NMe$_2$: 2.11 (s); SiMe$_3$: 0.05.

EXAMPLE 2

11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-trimethylsilyloxy-2α-fluoro 1.24 ml of a solution of potassium terbutylate in 0.97M THF were added at –12° C. to a solution of 668 mg of 11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-trimethylsilyloxy and 6.7 ml of anhydrous THF. The mixture was stirred for 5 minutes and then 378 mg of N-fluoro dibenzene-sulfonimide were added. The mixture was stirred for 10 minutes at –12° C. and the reaction mixture was allowed to return to ambient temperature for 90 minutes. Isolation and purification operations were carried out to obtain 695 mg of the desired product.

NMR 250 MHz CDCl$_3$: H$_{11}$ (s): 6.42; H$_{13}$ (dd): 4.85; 6-OMe: 2.55 (s), N(Me)$_2$: 2.12 (s); CH$_3$—C—F (d): 1.60 J=22 Hz.

Preparation of the Starting Product of Example 2

Stage A: 11-deoxy-10,11-didehydro-3-de[(2,6-dideoxy-3-C-methyl-3-0-methyl-α-L-ribohexopyranosyl)-oxy]-6-0-methyl-3-oxo-erythromycin.

A mixture of 8.722 g of 11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-acetoxy-(described in European Patent No. 596,802) and 350 ml of anhydrous methanol were stirred for 44 hours, followed by evaporating, taking up in methylene chloride and drying to obtain 8.794 g of the desired product.

NMR 250 MHz CDCl$_3$: H$_{11}$ (s): 6.64; H$_{13}$ (dd): 4.99; H'$_1$: 4.25(d); 6-OMe (s): 2.87, 10 Me (s): 1.96 (s); N(Me)$_2$ (s): 2.25.

Stage B: 11-deoxy-10,11-didehydro-3-de[2,6-dideoxy-3-C-methyl-3-0-methyl-α-L-ribohexopyranosyl)-oxy]-6-0-methyl-3-oxo-erythromycin-2'-trimethylsilyloxy.

A mixture of 3.08 g of the product of the preceding stage, 340 mg of imidazole, 32 ml of anhydrous THF and 1.06 ml of hexamethyldisilylazane was stirred for 4 days at ambient temperature, followed by evaporation to dryness. The residue was taken up in a mixture of 60 ml of methylene chloride and 60 ml of 0.5M sodium acid phosphate. The reaction mixture was stirred for 15 minutes, followed by decanting, extraction with methylene chloride, drying and evaporating to dryness to obtain 3.345 g of the desired product.

NMR 250 MHz CDCl$_3$: H$_{11}$: 6.61 (s); H$_{13}$ (dd): 4.92; 6OMe (s): 2.85; N(Me)$_2$: 2.15 (s): SiMe$_3$ (s): 0.02.

EXAMPLE 3

11-deoxy-10,11-didehydro-3-de[2,6-dideoxy-3-C-methyl-3-0-methyl-α-L-ribohexopyranosyl)-oxy]-6-0-methyl-3-oxo-erythromycin-2'-acetoxy-2α-fluoro 2.5 ml of a solution of potassium terbutylate in the THF (0.97M) were added at −8° C. to a suspension of 1.224 g of 11-deoxy-10,11-didehydro-3-de[(2,6-dideoxy-3-C-methyl-3-0-methyl-α-L-ribohexopyranosyl)-oxy]-6-0-methyl-3-oxo-erythromycin-2'-acetoxy (EP 596,802) and 10 ml of anhydrous THF. 756 mg of N-fluorodibenzene-sulfonimide were added and the mixture was stirred for 1 hour at −5° C. Then, 10 ml of saturated bicarbonated water and 10 ml of ethyl acetate were added, and the mixture was stirred for 10 minutes at ambient temperature, followed by filtering, rinsing, decanting, washing with water, reextraction with ethyl acetate, washing, drying and filtering. Chromatography on silica was carried out eluting with a methylene chloride-methanol mixture with 8% concentrated ammonium hydroxide 95-5 to obtain 623 mg of the desired product.

NMR: H$_{11}$: 6.47 (s); H$_{13}$: 5.03 (dd); 6-OMe: 2.66 (s); N—Me$_2$: 2.25 (s): CH$_3$—C—F: 1.75 (d) J=21.5 Hz.

Use of 11,12-dideoxy-3-de[(2,6-dideoxy-3-C-methyl-3-0-methyl-α-L-ribohexopyranosyl)-oxy]-2α-fluoro-6-0-methyl-3-oxo-12,11-[oxycarbonxyl-[4-[4-(3-pyridinyl)-1H-imidazol-1-yl]-butyl]-imino]-erythromycin A Stage A: 11-deoxy-10,11-didehydro-3-de[(2,6-dideoxy-3-C-methyl-3-0-methyl-α-L-ribohexopyranosyl)-oxy]-6-0-methyl-3-oxo-erythromycin-2α-fluoro.

A mixture of 5.476 g of the product of Example 2, 50 ml of THF and 11.2 ml of 1M tetrabutylammonium fluoride in THF was stirred for 3 hours 30 minutes and the solvent was evaporated off. 37 ml of ethyl acetate, 37 ml of water and 7.5 ml of 20% ammonium hydroxide were added thereto and the mixture was stirred for 10 minutes, followed by decanting, extraction with ethyl acetate, drying and filtering. The filtrate was concentrated to dryness and the product obtained was chromatographed on silica eluting with a CH$_2$Cl$_2$—MeOH ammonium hydroxide mixture 99-1, then 98-2, 97-3, 96-4, 95-5 to obtain 2.452 g of the desired product.

Stage B: 11-deoxy-10,11-didehydro-3-de[(2,6-dideoxy-3-0-methyl-α-L-ribohexopyranosyl)-oxy]-6-0-methyl-3-oxo-erythromycin-2'-acetoxy-2α-fluoro.

1.02 g of the product of Stage A, 10 ml of methylene chloride and 241 μl of acetic anhydride were stirred for 3 hours. After evaporation, 10 ml of water and 10 ml of ethyl acetate were added and the reaction mixture stood for 1 hour at ambient temperature with stirring followed by decanting, drying and evaporation to obtain 1.01 g of the desired product.

TLC SiO$_2$ dichloromethane 95—MeOH 5 ammonium hydroxide, rf: 0.14.

NMR 250 MHz CDCl$_3$: H$_{11}$ (s): 6.47; H'$_2$ (q): 4.75; N(Me)$_2$ (s): 2.22; CH$_3$—CO—O (s): 2.05; CH$_3$—C—F (d): 1.75; J=22 Hz.

Stage C: 12-(oxycarbonylimidazol)-11-deoxy-10,11-didehydro-3-de-[(2,6-dideoxy-3-C-methyl-3-0-methyl-α-L-ribohexopyranosyl)-oxy]-6-0-methyl-3-oxo-erythromycin-2'-acetoxy-2α-fluoro.

0.388 g of carbonyldiimidazole and 24 μl of DBU were added at 0° C. to a solution of 1.01 g of the product of the preceding stage and 10 ml of anhydrous THF. The THF was evaporated off and 10 ml of water and 10 ml of ethyl acetate were added. The reaction mixture was stirred for 10 minutes, followed by extraction, drying and evaporation to obtain 0.902 g of crude product which was chromatographed eluting with an ethyl acetate—triethylamine mixture 96-4 to obtain 0.573 g of the desired product.

NMR CDCl$_3$): H$_{11}$: 6.69 (s); H$_{13}$: 5.55 (dd); 6-OMe: 2.62 (s); N—Me$_2$: 2.25 (s): 10-Me: 1.90 (s).

Stage D: 2'-acetoxy-11,12-dideoxy-3-de[(2,6-dideoxy-3-C-methyl-3-0-methyl-α-L-ribohexopyranosyl)-oxy]-2α-fluoro-6-0-methyl-3-oxo-12,11-[oxycarbonyl-[4-[4-(3-pyridinyl)-1H-imidazol-1-yl]-butyl]-imino]-erythromycin A.

211 mg of 4-(3-pyridinyl) 1H-imidazol-1-butylamine, 573 mg of the product of the preceding stage and 5 ml of anhydrous THF were added together at 0° C. and then 19 μl of DBU were added. The reaction mixture was kept in a refrigerator overnight. After evaporation, 10 ml of ethyl acetate and 10 ml of water were added and the mixture was stirred for 10 minutes, followed by extraction, drying and evaporation to obtain 0.545 g of crude product which was used as it is for the following stage.

Stage E: 11,12-dideoxy-3-de[[(2,6-dideoxy-3-C-methyl-3-0-methyl-α-L-ribohexopyranosyl)-oxy]-2α-fluoro-6-0-methyl-3-oxo-12,11-[oxycarbonyl-[4-[4-(3-pyridinyl)-1H-imidazol-1-yl]-butyl]-imino]-erythromycin A.

The preceding product was taken up in methanol and the reaction mixture was stirred at ambient temperature for 24 hours. The product obtained was chromatographed on silica eluting with an ethyl acetate—triethylamine mixture 96-4 to obtain after evaporation, 189 mg of the desired product.

Various modifications of the compounds and process of the invention may be made without departing from the spirit or scope thereof and it is to be understood that the invention is intended to be limited only as defined in the appended claims.

What we claim is:
1. A compound selected from the group consisting of a compound of the formula

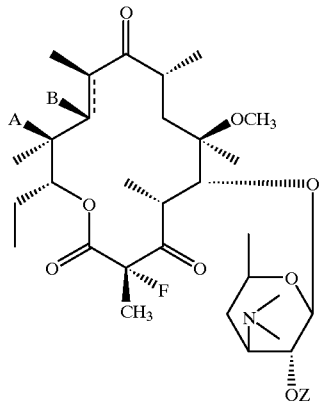

I wherein A is —OH and B forms with the 10-carbon a carbon—carbon double bond or A and B together form a carbonate, Z is trimethylsilyl and its non-toxic, pharmaceutically acceptable acid addition salts.

2. A compound having the formula

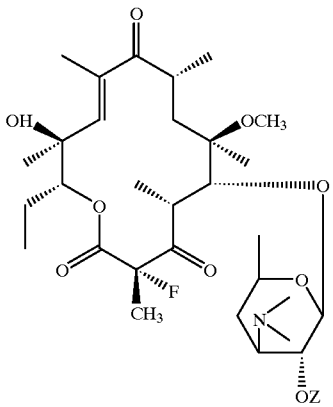

I_A wherein —OZ is selected from the group consisting of —OH, etherified hydroxy or esterified hydroxy and its non-toxic, pharmaceutically acceptable acid addition salts.

3. A compound of claim 1 having the formula

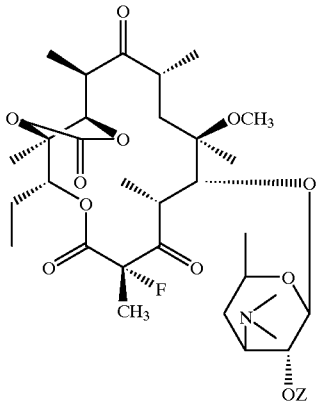

I_B wherein Z is defined as in claim 2.

4. A process for the preparation of a compound of the formula

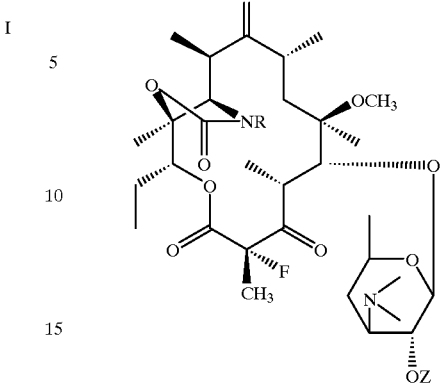

III wherein A and B are as defined in claim 1 and —OZ is selected from the group consisting of —OH, etherified hydroxy or esterified hydroxy and its non-toxic, pharmaceutically acceptable acid addition salts comprising reacting a compound of claim 1 with carbonyldiimidazole to obtain a compound of the formula

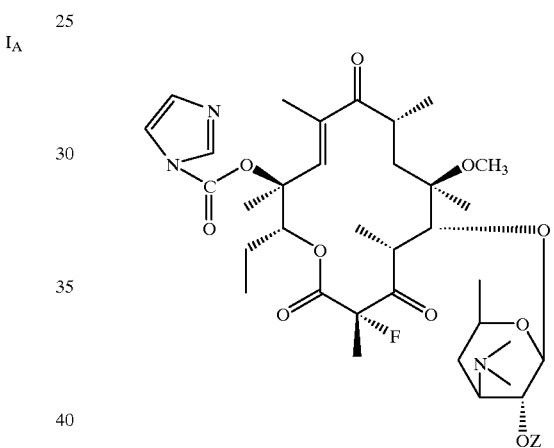

II reacting the latter with an amine of the formula H$_2$NR wherein R is alkyl of 1 to 6 carbon atoms to obtain the compound of formula III and optionally releasing the 2'-hydroxyl.

5. A compound of the formula

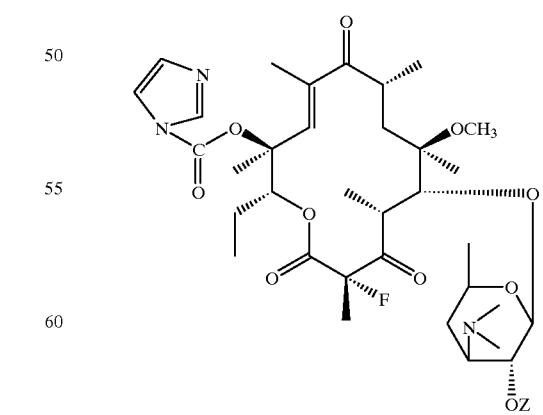

II wherein —OZ is defined as in claim 2.

* * * * *